United States Patent
Rogers et al.

(10) Patent No.: US 6,258,023 B1
(45) Date of Patent: Jul. 10, 2001

(54) DEVICE AND METHOD FOR ISOLATING A SURFACE OF A BEATING HEART DURING SURGERY

(75) Inventors: Danny Carpenter Rogers, Athens; Samuel Lynn Austin, Eustace; Albert Davis, Richardson, all of TX (US)

(73) Assignee: Chase Medical, Inc., Richardson, TX (US)

( * ) Notice: Subject to any disclaimer, the term of this patent is extended or adjusted under 35 U.S.C. 154(b) by 0 days.

(21) Appl. No.: 09/376,538

(22) Filed: Aug. 18, 1999

Related U.S. Application Data
(60) Provisional application No. 60/143,023, filed on Jul. 9, 1999.

(51) Int. Cl.[7] ............... A61F 2/00; A61B 17/00
(52) U.S. Cl. ................................ 600/37; 600/201
(58) Field of Search .................. 600/37, 201, 205, 600/208, 210, 213, 215, 226, 227, 228, 229, 231, 232, 233, 234, 235, 214; 128/897, 898; 606/1, 191, 205–208

(56) References Cited

U.S. PATENT DOCUMENTS

| | | |
|---|---|---|
| 3,503,398 | 3/1970 | Fogarty et al. . |
| 3,515,129 | 6/1970 | Truhan . |
| 3,983,863 | 10/1976 | Janke et al. . |

(List continued on next page.)

FOREIGN PATENT DOCUMENTS

| | | |
|---|---|---|
| 0 630 629 A1 | 12/1994 | (EP) . |
| 0 791 330 A2 | 8/1997 | (EP) . |
| 0 820 721 A1 | 1/1998 | (EP) . |
| 0 920 835 A1 | 6/1999 | (EP) . |
| 2 267 827 | 12/1993 | (GB) . |
| WO 94/14383 | 7/1994 | (WO) . |
| WO 95/15715 | 6/1995 | (WO) . |
| WO 95/17127 | 6/1995 | (WO) . |
| WO 96/00033 | 1/1996 | (WO) . |
| WO 97/10753 | 3/1997 | (WO) . |
| WO 98/17182 | 4/1998 | (WO) . |
| WO 98/27869 | 7/1998 | (WO) . |

OTHER PUBLICATIONS

"Mammary artery–coronary artery anastomosis as method of treatment for angina pectoris", Kolessov MD, Journal of Thoracic and Cardiovascular Surgery, vol. 54, No. 4, Oct. 1967, pp. 535–544.

"Direct coronary surgery with saphenous vein bypass without either cardiopulmonary bypass or cardiac arrest", Benetti, Official Journal of the International Society for Cardiovascular Surgery, vol. 26, No. 3, May–Jun. 1985, pp. 217–222.

A Prospective Evaluation of the Pulsatile Assist Device, Zumbro, Jr. MD et al., The Annals of Thoracic Surgery, No. 2, Aug. 1979, pp. 269–273.

(List continued on next page.)

Primary Examiner—Samuel G. Gilbert
(74) Attorney, Agent, or Firm—Haynes & Boone LLP

(57) ABSTRACT

Disclosed is a device for isolating a cardiac surgical site. The device includes a first finger having a clinging accessory for attaching the first finger to a heart, a second finger having a clinging accessory for attaching the second finger to the heart, a first joint disposed on the first finger so that the first finger may rotate on a surface of the heart such that the rotation stretches a surgical site, a first stopper disposed on the first finger for preventing undesired rotation of the first finger to isolate the surgical site, and a link for coupling the first finger to the second finger. Also disclosed is a method of isolating a cardiac surgical site. The method includes the steps of disposing a first finger on a heart, clinging the first finger to the heart surface, disposing a second finger on a heart, clinging the second finger to the heart surface, and then rotating the first finger for achieving selective isolation of the heart surface.

19 Claims, 3 Drawing Sheets

U.S. PATENT DOCUMENTS

| | | |
|---|---|---|
| 4,245,638 | 1/1981 | Lebeck et al. . |
| 4,492,229 | 1/1985 | Grunwald . |
| 4,635,636 | 1/1987 | Goldstein . |
| 4,726,356 | 2/1988 | Santilli et al. . |
| 4,834,090 | 5/1989 | Moore . |
| 4,854,318 | 8/1989 | Solem et al. . |
| 4,865,019 | 9/1989 | Phillips . |
| 4,925,443 | 5/1990 | Heilman et al. . |
| 4,973,300 | 11/1990 | Wright . |
| 4,989,587 | 2/1991 | Farley . |
| 5,037,428 | 8/1991 | Picha et al. . |
| 5,098,369 | 3/1992 | Heilman et al. . |
| 5,131,905 | 7/1992 | Grooters . |
| 5,167,223 | 12/1992 | Koros et al. . |
| 5,195,506 | 3/1993 | Hulfish . |
| 5,197,948 | 3/1993 | Ghodsian . |
| 5,300,087 | 4/1994 | Knoepfler . |
| 5,318,579 | 6/1994 | Chow . |
| 5,374,277 | 12/1994 | Hassler . |
| 5,381,788 | 1/1995 | Matula et al. . |
| 5,383,840 | 1/1995 | Heilman et al. . |
| 5,425,705 | 6/1995 | Evard et al. . |
| 5,437,651 | 8/1995 | Todd et al. . |
| 5,452,733 | 9/1995 | Sterman et al. . |
| 5,476,479 | 12/1995 | Green et al. . |
| 5,509,890 | 4/1996 | Kazama . |
| 5,514,075 | 5/1996 | Moll et al. . |
| 5,527,319 | 6/1996 | Green et al. . |
| 5,529,571 | 6/1996 | Daniel . |
| 5,613,937 | 3/1997 | Garrison et al. . |
| 5,727,569 | 3/1998 | Benetti et al. . |
| 5,749,892 | 5/1998 | Vierra et al. . |
| 5,782,746 | 7/1998 | Wright . |
| 5,807,243 * | 9/1998 | Vierra et al. ................. 600/204 |
| 5,836,311 | 11/1998 | Borst et al. . |
| 5,865,730 | 2/1999 | Fox et al. . |
| 5,885,271 | 3/1999 | Hamilton et al. . |
| 5,891,017 | 4/1999 | Swindle et al. . |
| 5,894,843 | 4/1999 | Benetti et al. . |
| 5,947,896 | 9/1999 | Sherts et al. . |
| 5,976,080 * | 11/1999 | Farascioni ................. 600/213 |
| 6,007,486 * | 12/1999 | Hunt et al. ................. 600/205 |
| 6,036,641 | 3/2000 | Taylor et al. . |
| 6,050,266 * | 4/2000 | Benetti et al. ................. 128/898 |
| 6,056,689 * | 5/2000 | Lenox et al. ................. 600/217 |
| 6,063,021 * | 5/2000 | Hossain et al. ................. 600/37 |
| 6,102,854 * | 8/2000 | Cartier et al. ................. 600/228 |

OTHER PUBLICATIONS

"Coronary Artery Operation with Support of the Hemopump Cardiac Assist System", Lonn MD, et al., The Society of Thoracic Surgeons, Dec. 1994, pp. 1–5.

"Coronary Artery Operation Supported by the Hemopump: An Experimental Study on Pig", Lonn MD, et al., The Society of Thoracic Surgeons, Dec. 1994, pp. 516–518.

"Enhanced preservation of Acutely Ischemic Myocardium With Transseptal Left Ventricular Assist", Fonger MD, et al., The Annals of Thoracic Surgery, vol. 57, No. 3, Mar. 1994, pp. 1–6.

"Delayed Recovery of Severely "Stunned" Myocardium With the Support of a Left Ventricular Assist Device After Coronary Artery Bypass Graft Surgery", Ballantyne MD, et al. Journal of the American College of Cardiology, Dec. 1987, pp. 1–3.

"Current Status of Cardiac Surgery: A 40 Year Review", Richenbacher MD, et al., Journal of the American College of Cardiology, Dec. 1989, pp. 535–544.

"Direct Myocardial Revascularization without Extracorporeal Circulation", Benetti MD, et al., Chest/100/2/Aug. 1991, pp. 313–316.

"To Use or Not to Use the Pump Oxygenator in Coronary Bypass Operation", Ankeney MD, The Annals of Thoracic Surgery, vol. 19, No. 1, Jan. 1975, pp. 108–109.

"Direct Myocardial Revascularization by Saphenous Vein Graft", Favaloro MD, et al., The Annals of Thoracic Surgery, vol. 10, No. 2, Aug. 1970, pp. 97–111.

"Direct Myocardial Revascularization without Cardiopulmonary Bypass", Buffolo et al., Thoracic Cardiovascular Surgeon, Dec. 1985, pp. 1–4.

"Coronary Artery Operation with Support of the Hemopump Cardiac Assist System", Lonn MD, et al., The Society of Thoracic Surgeons, Dec. 1994, pp. 1–5.

"Coronary Artery Operation Supported by the Hemopump: An Experimental Study on Pig", Lonn MD, et al., The Society of Thoracic Surgeons, Dec. 1994, pp. 516–518.

"Coronary Artery Revascularization without Cardiopulmonary Bypass", Archer DO, et al., Texas Heart Institute Journal, vol. 11, No. 1, Mar. 1984, pp. 52–57.

Coronary Artery Bypass Grafting Without Cardiopulmonary Bypass and Without Interruption of Native Coronary Flow using a Novel Anastomosis Site Restraining Device ("Octupus"), Borst MD, et al., American College of Cardiology, vol. 27, Dec. 1996, pp. 1356–1364.

"Coronary Artery Disease–Physiologic Concepts–Surgical Operation", Beck MD, Annals of Surgery, Apr. 1957, vol. 145, No. 4, pp. 439–460.

"Heart–mechanical Assist Device Interaction", Kresh, et al., vol. XXXII ASAIO Dec. 1986, pp. 437–443.

"Long–term Follow–up of Survivors of Postcardiotomy Circulatory Support", Ruzevich, et al., vol. XXXIV ASAIO Dec. 1988, pp. 116–124.

"Extended Clinical Support with an Implantable Left Ventricular Assist Device", McGee et al., vol. XXXV ASAIO Dec. 1989, pp. 614–616.

"Coronary Artery Bypass Without Cardiopulmonary Bypass", Pfister, MD, et al.,The Society of Thoracic Surgeons, Feb. 3–5, 1992, pp. 1086–1092.

"Reoperative Coronary Artery Bypass Grafting Without Cardiopulmonary Bypass", Fanning MD, et al.,The Society of Thoracic Surgeons Dec. 1993, pp. 486–489.

"Placement of Coronary Artery Bypass Graft Without Pump Oxygenator", Trapp MD, et al.,The Annals of Thoracic Surgery, vol. 19, No. 1, Dec. 1975, pp., 1–9.

Direct Mechanical Ventricular Actuation for Cardiac Arrest in Humans, Anstadt MD, et al.,57th Annual Scientific Assembly, San Francisco, Nov. 4–8, 1991, pp. 86–92.

"Transfemoral Placement of the Left Ventricular Assist Device "Hemopump" During Mechanical Resuscitation", Scholz, et al., Thoracic and Cardiovascular Surgeon, vol. 28, Feb. 1990, pp., 69–72.

* cited by examiner

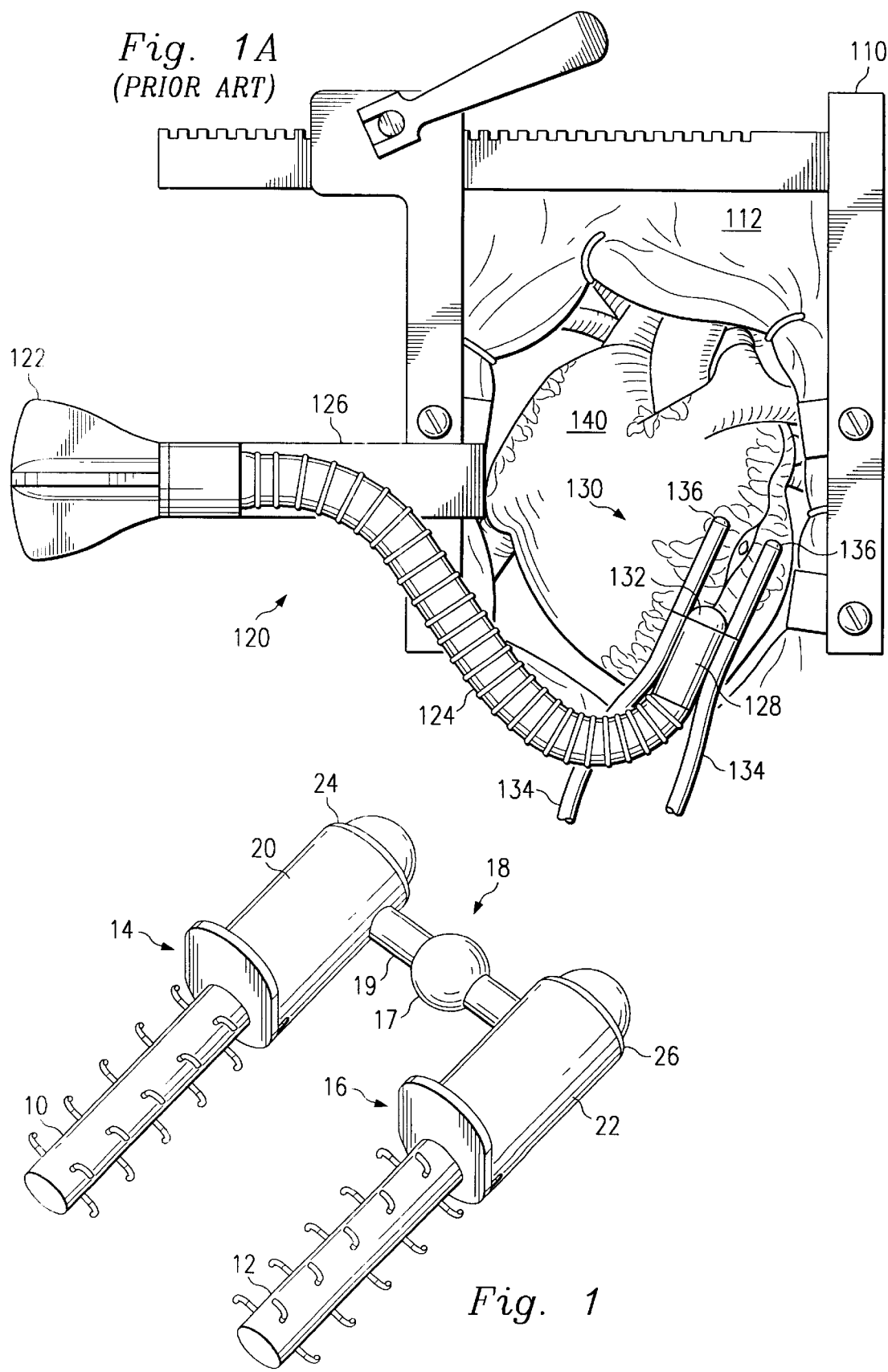

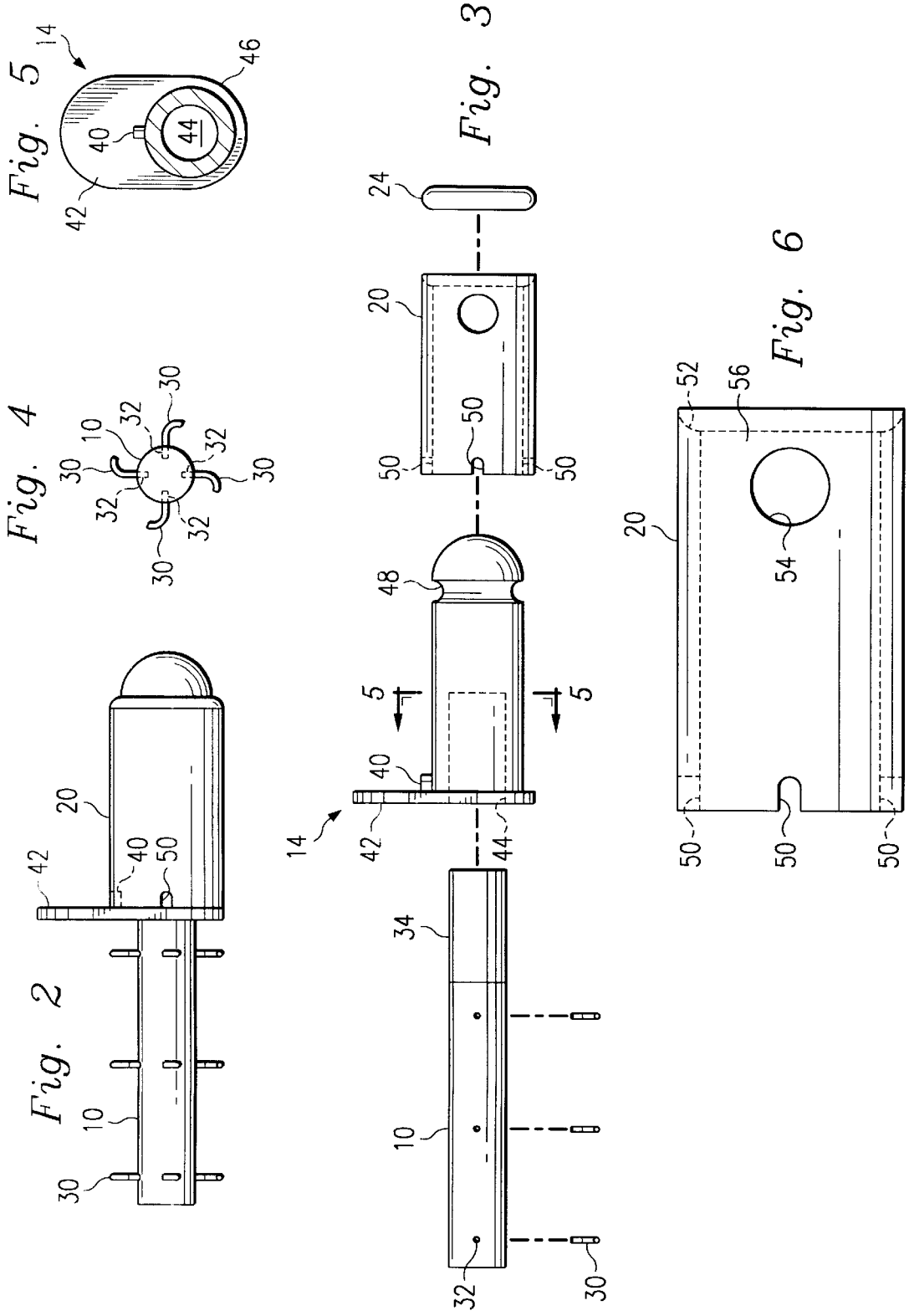

DEVICE AND METHOD FOR ISOLATING A SURFACE OF A BEATING HEART DURING SURGERY

This application claims priority under 35 USC§ 119(e)(1) of provisional application number 60/143,023 filed on Jul. 09, 1999.

FIELD OF THE INVENTION

The invention relates generally to medical surgical devices, and more particularly to a device and method of stabilizing a surgical site during cardiac or cardiovascular surgery.

BACKGROUND OF THE INVENTION

Heart disease and associated cardiovascular problems have become so common in the United States that over 400,000 open heart surgeries are performed each year. Traditionally, physicians would open the chest and stop the heart before performing a surgical procedure on the heart. However, medical practices have improved, and physicians now recognize that there are advantages to performing surgery on a beating heart. For example, performing surgery on a beating heart avoids the necessity to expose the heart to filters, oxygenators, tubes, and other devices. This decreases the trauma associated with stopping the heart, as well as avoids other dangers that stopping the heart poses to a patient. In addition, by avoiding the use of these devices, the physician can lower the expense of an operation. Furthermore, performing surgery on a beating heart lowers the risk of ischemic damage to heart and surrounding tissue.

Unfortunately, there are many difficulties and challenges which must be overcome to successfully perform surgery on a beating heart. For example, every time the heart beats, the heart moves. This makes it difficult to isolate a specific site on the heart for surgery. Furthermore, physicians typically must develop great skill and expertise to accommodate the movement of the heart with existing instruments which were designed for use with a heart that is stopped. Because of the increased demands of performing surgery on a beating heart, surgery on a beating heart often takes longer than surgery on a stopped heart. Fortunately, devices and methods are being developed which decrease the amount of time and expertise it takes to identify and isolate a target vessel and thus, reduce the time it takes to perform open heart surgery.

One family of instruments which have been developed to facilitate surgery on a beating heart are known as cardiac immobilization devices (devices). A number of these devices function by attaching to the heart at two or more points. The points are then moved further apart, thus stretching the surface area of the heart about which surgery is to be performed (surgical site). The devices typically grip the heart surface by suction. Unfortunately, there are a number of disadvantages associated with these methods of isolating a surgical site.

Some cardiac immobilization devices often appear to be little more than steak tongs or clamps which have been slightly altered to attach to a heart surface. Other devices use flex links or rods to attach to a retractor and then use a metallic foot to stabilize the heart surface. Suction devices may comprise a plurality of suction cups, or may have at least one hollow cylinder with holes in it, which is then attached to a pump which pulls a vacuum at the holes.

FIG. 1A (prior art) shows a cardiac immobilization device 130 attached to a heart surface 140. To perform open heart surgery, typically a chest retractor 110 is braced within a rib cage and used to maintain an opening in the chest wall 112 which provides access to the heart surface 140. A stabilizing member, such as a flexible arm assembly 120 is used to securely locate a cardiac immobilization device 130 upon the heart surface 140. Accordingly, the stabilizing member 120 is coupled to the retractor 110 via a clamp 126 and holds the cardiac immobilization device 130 in a predetermined position.

The flexible arm assembly 120 includes a flexible arm 124 which may be bent and twisted into various shapes and geometries to access different locations on the heart surface 140. At the end of the flexible arm 124 closest to the heart surface 140 is a socket 128 for attaching the flexible arm 124 to the cardiac immobilization device 130. At the other end of the flexible arm 124 is a handle 122 which when turned tightens a cable (not shown) within the flexible arm 124. The tightening of the cable makes the flexible arm 124 rigid and immobile. The tightening of the cable also tightens the socket 128, allowing the socket 128 to grip an object, such as a ball 132 (the ball 132 is part of the cardiac immobilization device 130).

The shown cardiac immobilization device 130 uses suction to attach to a surface of the heart 140. To attach the cardiac immobilization device 130 to the heart surface 140, the cardiac immobilization device 130 utilizes a foot plate 136 with holes thereunder (not shown) on which a vacuum is placed. The vacuum is maintained by air hoses 134 which are attached to an air pump (not shown) and the foot plate 136. Thus, the cardiac immobilization device 130 is held stationary on the heart surface 140 at the end of the flexible arm 124 of the flexible arm assembly 120 so that the heart surface 140 located within the foot plate 136 can be isolated.

One disadvantage of many tong type attachments is that they provide an uneven spread (the heart surface closest to the tong's hinge point is spread a smaller distance than the heart surface at the end of the tong).

There are also many disadvantages associated with using suction to isolate a surgical site. For example, many patients have a heart which is surrounded with fatty tissue. Since the fat surrounding the heart moves, when a physician uses a suction device to isolate a heart surface, the suction cups or suction holes attach to the fat (rather than the heart surface). The operative result of the device attaching to the fatty tissue is that the heart surface can still beat underneath the fatty tissue, which means that isolation and stabilization of the surgical site is poor. Furthermore, the fatty tissue may be drawn into the device (at a hole, for example) by the suction, and may clog the suction device thereby stopping suction at the holes which are further along and at the end of the device. In addition, after attachment to the heart is made with a suction device, the ability to spread the heart surface is limited by the force of suction on the heart surface. Should the suction break, the device must be repositioned and reattached to the heart, which consumes time and is a nuisance to the physician. Furthermore, when strong enough suction is applied to the heart surface to achieve adequate spreading and to prevent slippage, the suction can cause blood to accumulate and clot just beneath the heart surface, a hematoma (this condition is also commonly referred to as a "heart hickie").

Therefore, what is needed is a device and method of isolating a surgical site for cardiac and cardiovascular surgery. The device should contact a minimal surface of the heart, accommodate the non-planar geometry of the heart, grip the heart firmly, yet gently, and should be easy to apply to and to remove from a beating heart. The present invention provides such a device and method.

SUMMARY OF THE INVENTION

The present invention provides a device and method for isolating a heart surface, particularly, the surface of a beating heart during cardiovascular surgery. The device utilizes rotation to attach to the heart surface and then spread the heart which isolates the spread portion of the heart for surgery.

Disclosed is a device for isolating a cardiac surgical site. The device generally comprises a first finger (which may be cylindrical) having a clinging accessory for attaching the first finger to a heart. Furthermore the device could comprise a second finger having a clinging accessory for attaching the second finger to the heart, a first joint disposed on the first finger so that the first finger may rotate on a surface of the heart such that said rotation stretches a surgical site, and a link for attaching the first finger to the second finger. In addition, a first stopper may be disposed on the first finger for preventing undesired rotation of the first finger to isolate the surgical site.

The accessory for attaching could comprise a plurality of tines, a plurality of suction points, or a rough textured surface such as a surface similar to sandpaper, for example. In addition, the first joint or a second joint (disposed on the second finger) could comprise a rotatable handle coupled in a sleeve. Furthermore, the first stopper or a second stopper (disposed on the second finger) could be configured such that the rotatable handle comprises at least one notch and the sleeve has at least one rib. Likewise, the first stopper or the second stopper (disposed on the second finger) could be configured such that the rotatable handle comprises at least one rib and the sleeve has at least one notch. The handle could comprise an O-ring groove for securing an O-ring about an end of the handle.

The link could comprise a ball and socket joint disposed between the first finger and the second finger for providing multi-axis articulation of the first finger and the second finger, as well as a first attachment bar coupled between the first handle and the ball and socket joint, and a second attachment bar coupled between the second handle and the ball and socket joint. Conversely, the link could comprise a first ball and socket joint associated with the first handle, a second ball and socket joint associated with the second handle, and an attachment bar for coupling the first ball and socket joint to the second ball and socket joint.

More generally, the present invention provides a means for isolating a cardiac surgical site. The means for isolating comprises a first support means, such as a finger or a functional equivalent, having a clinging means for attaching the first support means to a heart, and a second support means, such as a second finger or a functional equivalent, having a clinging means for attaching the second support means to the heart. The means for isolating also includes a rotating means, such as a cylinder or a functional equivalent, disposed on the first support means so that the first support means may rotate on a surface of the heart, a locking means, such as a rib and notch, or a functional equivalent, disposed on the first support means for preventing undesired rotation of the first support means. An attaching means, such as a link or a functional equivalent, connects the first support means to the second support means.

In another embodiment, the present invention provides a method of isolating a cardiac surgical site. The method comprises disposing a first finger on a heart, clinging the first finger to the heart surface, disposing a second finger on a heart, clinging the second finger to the heart surface, and rotating the first finger for achieving selective isolation of cardiac tissue. The method may further comprise rotating the second finger, locking the first finger to prevent rotation, or locking the second finger to prevent rotation. The method may also provide that clinging comprises penetrating the surface of the heart, applying suction to the surface of the heart, or applying an abrasive surface for frictionally gripping the surface of the heart. In addition, when applying a finger, the method may further comprise the step of compressing the finger onto the heart surface. Furthermore, the method could include the step of elevating the finger while maintaining its attachment to the heart surface.

The rotational action of the present invention allows the physician to overcome problems associated with fatty tissue on the heart surface, to adjust the spread of the heart surface during surgery, and to attach and detach the present invention from the heart quickly.

BRIEF DESCRIPTION OF THE DRAWINGS

Other aspects of the invention, including specific embodiments, are understood by reference to the following detailed description taken in conjunction with the drawings in which:

FIG. 1A (prior art) shows a cardiac immobilization device attached to a heart surface;

FIG. 1 is an isometric view of one embodiment of a device according to the teachings of the present invention;

FIG. 2 shows a side view of the device shown in FIG. 1;

FIG. 3 is an exploded view of one arm of the device of FIG. 1;

FIG. 4 is a front view of the finger having tines attached to the holes;

FIG. 5 is a cut rear view of the handle taken along line 5—5 of FIG. 3;

FIG. 6 shows the sleeve in greater detail;

Figure 7:
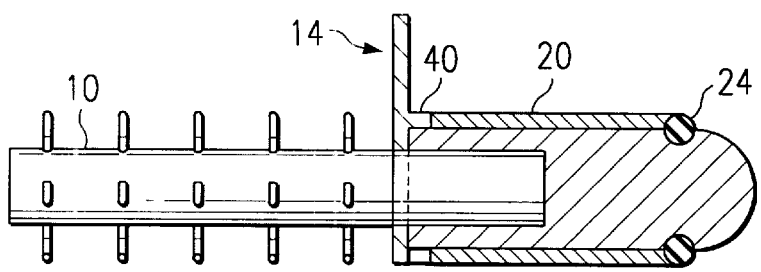
FIG. 7 is a cut side view of an arm in a locking position where the locking position is defined as the position of the device when the rib is set in a notch.

References in the detailed description correspond to like references in the figures unless otherwise indicated.

DETAILED DESCRIPTION OF THE PREFERRED EMBODIMENT

The present invention provides devices and methods for isolating a heart surface, and particularly the surface of a beating heart, during cardiovascular surgery. The device attaches to the heart surface and then utilizes rotation to spread the heart and isolate the spread portion of the heart (surgical site) for surgery. The rotational action of the present invention allows the physician to overcome problems associated with fatty tissue on the heart surface, to adjust the spread of and tension on the surgical site during surgery, and to attach and detach the device from the heart quickly. Other advantages and uses of the present invention will be apparent to those of ordinary skill in the art from the following description of the drawings.

FIG. 1 is an isometric view of one embodiment of a device according to the teachings of the present invention. The device generally comprises a pair of stainless steel fingers 10, 12 which are mounted in stainless steel handles 14, 16. Of course, the fingers 10, 12 and the handles 14, 16 may be made of any other material, such as plastics, rubber, other metals, or composite materials, for example. Furthermore, the fingers 10, 12 and the handles 14, 16 could be formed, cut or molded as a single unit. Stainless steel sleeves 20, 22 fit over the handles 14, 16 and are held in place about the handles 14, 16 by resilient O-rings 24, 26. The combination of a finger, a handle, a sleeve, and an O-ring is called an "arm." To couple two arms together, the sleeves, 20, 22 are attached together by a link 18 which is shown in FIG. 1 as a ball and socket assembly, for example.

A link is any device or collection of devices used to associate a finger and a stabilization device, such as another finger. The link 18 of FIG. 1 comprises a stainless steel ball 17, which is weldedly coupled to each sleeve 20, 22 by stainless steel attachment bars 19. The ball 17 is securely fastened in a socket 128 of the flexible arm assembly 120 shown in figure Ia. Of course, other link devices may be used. For example, the link 18 could comprise an attachment bar alone. Likewise, stabilizing members may have a variety of designs, and these other designs may use other types of mechanical links to maintain a predetermined distance between the fingers.

FIG. 2 shows a side view of the device illustrated in FIG. 1. Finger 10 has a plurality of tines 30 which function as a clinging accessory to attach the device to a heart surface. Accordingly, a clinging accessory provides a finger traction to a heart surface. Other clinging accessories (such as suction holes, suction cups, rough textured surfaces (such as sandpaper), barbs, or electrostatic attachment, for example) are well known in the art and may be adapted for use with the present invention. Also, the handle 14 has a knob 42 which extends higher than the sleeve 20 so that the physician may grasp and rotate the handle 14. The sleeve 20 has a plurality of notches 50, and the handle 14 has a rib 40 which fits securely inside of one notch 50. Accordingly, the combination of the rib 40 and a notch 50 together form a stopper which may be set to prevent rotation of the fingers 10, 12 as discussed below. A better understanding of the form and function of the present invention may be gained by examining the devices' individual components and their interrelations.

FIG. 3 is an exploded view of one arm of the device of FIG. 1. In FIG. 3, the finger 10 is seen to possess a plurality of holes 32 which accept the tines 30. Although three holes 32 and three tines 30 are shown in FIG. 3, it should be understood that the finger 10 may have any number of holes 32 and a corresponding number of tines 30. The holes 32 are of sufficient depth so that the tines 30 may be attached therein with solder, glue or by other means. Although the finger 10 of FIG. 3 is shown to be cylindrical, it should be understood that a finger may have any geometry so long as it may attach to a heart surface and stretch a surgical site by rotating. Finger 10 also has an attachable portion 34 which fits securely in a cylinder 44 of the handle 14.

The handle 14 has a grippable knob 42 which is capable of being securely grasped and turned. Abutting the grippable knob 42 is the rib 40. At the other end of the handle 14 is a groove 48 which functions as an O-ring seat. The end of the handle 14 having the groove 48 is preferably shaped like a hemisphere to facilitate placing the O-ring 24 onto the groove 48.

FIG. 4 is a front view of the finger 10 having tines 30 attached and holes 32. From FIG. 4 it is seen that the tines 30 have a hook shape which minimizes heart surface penetration and which facilitates the release of the tines from the heart muscle. The tines are of a stiffness so that should a stretching rotation require the releasing of the tines from the heart surface, they may release without ripping the heart surface, and then re-penetrate the heart surface at a new location, if necessary. Also, it should be noted that the tines point generally in the direction of the grabbing rotation. Although four linear rows are shown in FIG. 4, the invention may have any number of rows which may include non-linear, or even apparently random, row formations. In one embodiment, the tines have a length of about one quarter inch. Of course, other methods of attachment are well known in the art. These include but are not limited to, rough textured surfaces such as sandpaper, barbs, electrostatics, and suction holes, for example.

FIG. 5 is a cut rear view of the handle 14 taken along line 5—5 of FIG. 3. From this view it can be seen that the grippable knob 42 extends both above and below the cylinder 44. The portion of the grippable knob 42 extending below the cylinder 44 forms a lip 46 which is of a width that matches the circumference of the sleeve 20 such that when the sleeve 20 fits over the cylinder 44 the outside of the lip 46 aligns with the outside of the sleeve 20. This view also illustrates that the rib 40 is of a width and size to accommodate the notch 50.

FIG. 6 shows the sleeve 20 in greater detail. As shown, sleeve 20 has a plurality of notches 50. Although four notches are shown in FIG. 6, the sleeve 20 may have any number of notches 50 so that the rotation of the fingers may be held at varying degrees of rotation. In addition, one side of the sleeve 20 has a hole 54, or other surface preparation, for accepting the attachment bar 19 (of course, the sleeve 20 may have other apertures attached to it depending on the link 18 used; likewise, the sleeve 20 may be connected to a link via welding, which avoids the need for apertures or modifications). The O-ring 24 pushes against the handle 14 so as to apply tension to the sleeve 20 to securely force a rib 40 over notch 50, as described below. Accordingly, the sleeve 20 has a cylinder 56 which at the end opposite the notches 50 has a tapered lip 52 which is shaped to accept the O-ring 24 to minimize wear on the O-ring 24.

FIG. 7 is a cut side view of an arm in a locking position where the locking position is defined as the position of the device when the rib 40 is set in a notch 50. Also, when in the locking position, the sleeve 20 fits securely against the handle 14. In the locking position, the O-ring 24 in groove 48 exerts a force upon the sleeve 20 to keep it in place abutting the handle 14. Furthermore, note that the rib 40 also abuts the sleeve 20, indicating that a notch 50 (not shown) is in position about the rib 40, forming a stopper.

Figure 8:
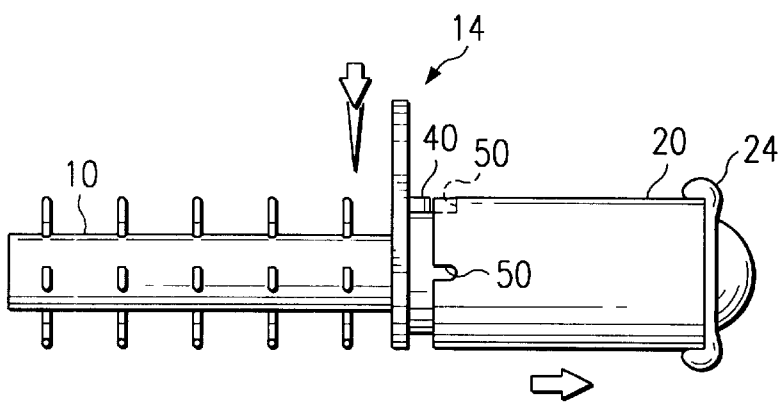
FIG. 8 illustrates the sleeve relative to the handle when the device is in a rotatable position.

FIG. 8 illustrates the sleeve 20 relative to the handle 14 when the device is in a rotatable position. Here, it can be seen that the sleeve 20 is pushed against the O-ring 24, causing distortion of the O-ring 24. The separation of the sleeve 20 from the grippable knob 42 removes the notch 50 from the rib 40 and allows for the handle 14 to be rotated. Accordingly, as the handle 14 rotates so does the finger 10. Then, depending on the direction of the rotation, the heart surface will either be stretched or compressed.

Figure 9:
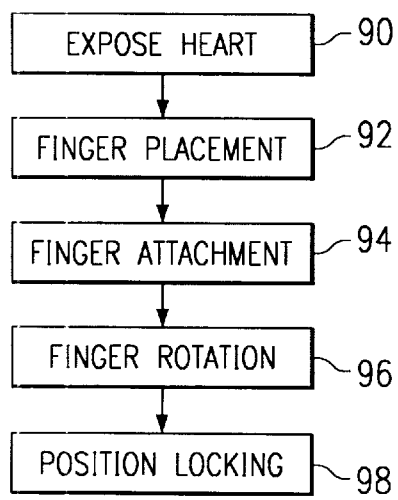
FIG. 9 is a flow diagram of one method of practicing the present invention.

One method of implementing the present invention uses the above disclosed device. Accordingly, FIG. 9 is a flow diagram of one embodiment of a method according to the present invention. First, the chest cavity is cut and opened and held securely in place, typically by a chest retractor, in an expose heart and place retractor step 90. As advances in open heart surgery are made, less intrusive means of exposing the heart for surgery will be developed and this method should in no way be read to limit its use to open chest cavities, or in the use of retractors.

Following the securing of the chest retractor, a flex arm with a finger 10 attached thereto is attached to the retractor in a fix flex arm step 91. Next, the finger 10 is placed about the area of the heart on which surgery is to be performed in a finger placement step 92. Then, the finger 10 is attached to the heart in a finger attachment step 94 and in a make flex arm rigid step 95, the flex arm is made stiff, typically by tightening a knob attached to the flex arm.

The fingers 10, 12 may be placed together on the heart in a single finger placement step 92 and then attached to the heart in a single finger attachment step 94, or each finger 10, 12 may be placed on the heart surface, and then attached to the heart surface independently of each other. In any event, the result is that the finger 10 lies on one side of the surgical site, and a second finger 12 lies generally on the opposite side of the surgical site. Optionally, to achieve better traction in a following rotation step, and thus better isolation of the heart surface, the fingers 10,12 may be gently pressed onto the heart (the fingers do not penetrate the heart surface).

Next, in a finger rotation step 96, at least one finger is rotated in a direction which increases the surface tension of the heart surface across the surgical site until a desired tension is achieved across the surgical site area. Once the desired tension is achieved on the heart surface, the tension is maintained by locking the device in that current state of rotation in a position locking step 98. Yet even better heart surface isolation may be achieved at this point by lifting the fingers 10, 12 (and thus the isolated heart surface) slightly. Surgery may then be performed at the isolated surgical site on the heart as well as on any veins or arteries going to or from the surgical site. If necessary, during surgery, the handles may be rotated in either a gripping or releasing direction to increase or decrease the tension at the surgical site. Then, after the surgery is completed, the above detailed steps may be reversed and the device removed.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

We claim:

1. A device for isolating a cardiac surgical site, comprising:
    a first finger having a clinging accessory adapted to attach the first finger to a heart, wherein the first finger is cylindrical; and
    a first joint disposed on the first finger adapted such that the first finger may rotate on a surface of the heart such that said rotation stretches the surgical site.

2. A device for isolating a cardiac surgical site, comprising:
    a first finger having a clinging accessory adapted to attach the first finger to a heart; and
    a first joint disposed on the first finger adapted such that the first finger may rotate on a surface of the heart such that said rotation stretches the surgical site, wherein the first joint comprises a rotatable handle coupled to a sleeve, and
    a first stopper disposed on the first finger for preventing undesired rotation of the first finger to isolate the surgical site, wherein the first stopper is configured such that the rotatable handle comprises at least one notch and the sleeve has at least one cooperating rib.

3. A device for isolating a cardiac surgical site, comprising:
    a first finger having a clinging accessory adapted to attach the first finger to a heart; and
    a first joint disposed on the first finger adapted such that the first finger may rotate on a surface of the heart such that said rotation stretches the surgical site, wherein the first joint comprises a rotatable handle coupled to a sleeve, and
    a first stopper disposed on the first finger for preventing undesired rotation of the first finger to isolate the surgical site, wherein the first stopper is configured such that the rotatable handle comprises at least one rib and the sleeve has at least one cooperating notch.

4. A device for isolating a cardiac surgical site, comprising:
    a first finger having a clinging accessory adapted to attach the first finger to a heart; and
    a first joint disposed on the first finger adapted such that the first finger may rotate on a surface of the heart such that said rotation stretches the surgical site, and a second finger having a clinging accessory adapted to attach the second finger to the heart, further comprising a second joint disposed on the second finger adapted such that the second finger may rotate on a surface of the heart.

5. A device for isolating a cardiac surgical site, comprising:
    a first finger having a clinging accessory adapted to attach the first finger to a heart;
    a first joint disposed on the first finger adapted such that the first finger may rotate on a surface of the heart such that said rotation stretches the surgical site,
    a second finger having a clinging accessory adapted to attach the second finger to the heart, and
    a link coupling the first finger to the second finger wherein the link comprises:
        a ball disposed between the first finger and the second finger adapted to secure attachment to a stabilizing member;
        a first attachment bar coupled between the first finger and the ball; and
        a second attachment bar coupled between the second finger and the ball.

6. A device for isolating a cardiac surgical site, comprising:
    a first finger having a clinging accessory adapted to attach the first finger to a heart;
    a first joint disposed on the first finger adapted such that the first finger may rotate on a surface of the heart such that said rotation stretches the surgical site,
    a second finger having a clinging accessory adapted to attach the second finger to the heart, and
    a link coupling the first finger to the second finger wherein the link comprises:
        a first stabilizing member associated with the first finger;
        a second stabilizing member associated with the second finger; and
        a retractor adapted to couple the first stabilizing member to the second stabilizing member.

7. A device for isolating a cardiac surgical site, comprising:
    a first finger having a clinging accessory adapted to attach the first finger to a heart,
    a first joint disposed on the first finger adapted such that the first finger may rotate on a surface of the heart such that said rotation stretches the surgical site, wherein the first joint comprises a rotatable handle coupled to a sleeve, and a first stopper disposed on the first finger for preventing undesired rotation of the first finger to isolate the surgical site, wherein the handle comprises an O-ring groove adapted to secure an O-ring about an end of the handle.

8. A method of isolating a cardiac surgical site, comprising the steps of:

disposing a first finger on a heart surface;

clinging the first finger to the heart surface;

disposing a second finger on the heart surface;

clinging the second finger to the heart surface; and rotating the first finger to achieve selective isolation of a portion of the heart surface.

9. The method of claim 8 further comprising the step of rotating the second finger to further achieve the selective isolation of the portion of the heart surface.

10. The method of claim 9 wherein the step of rotating the first finger and the step of rotating the second finger are accomplished at approximately the same time.

11. The method of claim 8 further comprising the step of compressing the first finger into the heart surface.

12. The method of claim 8 further comprising the step of lifting the first finger while maintaining the cling to the heart surface.

13. The method of claim 8 further comprising the step of locking the first finger to prevent rotation.

14. The method of claim 8 further comprising the step of locking the second finger to prevent rotation.

15. The method of claim 8 wherein either of said clinging steps comprises penetrating the surface of the heart.

16. The method of claim 8 wherein either of said clinging steps comprises applying suction to the surface of the heart via the first finger and the second finger.

17. The method of claim 8 wherein either of said clinging steps comprises applying the first or second fingers having a rough textured surface adapted to frictionally grip the surface of the heart.

18. The method of claim 8 further comprising the step of compressing the first finger and the second finger into the heart surface.

19. The method of claim 8 further comprising the step of lifting the first finger and the second finger from the heart while maintaining the cling to the heart surface.

* * * * *